United States Patent [19]

Komatsu et al.

[11] Patent Number: 5,780,628
[45] Date of Patent: Jul. 14, 1998

[54] PROCESS FOR PRODUCING DIOXOQUINAZOLINES

[75] Inventors: Masashi Komatsu; Shinji Nishii; Hiroshi Ueda, all of Osaka, Japan

[73] Assignee: Sumitomo Chemical Company, Limited, Osaka, Japan

[21] Appl. No.: 791,551

[22] Filed: Jan. 31, 1997

[30] Foreign Application Priority Data

Feb. 1, 1996 [JP] Japan .................................. 8-016650

[51] Int. Cl.⁶ .................................................. C07D 239/96
[52] U.S. Cl. .................................................. 544/285; 514/259
[58] Field of Search .................................................. 544/285

[56] References Cited

U.S. PATENT DOCUMENTS

| | | | |
|---|---|---|---|
| 4,016,166 | 4/1977 | Noda et al. | 544/285 |
| 4,405,623 | 9/1983 | Ishikawa et al. | 544/285 |
| 4,734,419 | 3/1988 | Hashimoto et al. | 514/259 |
| 4,883,800 | 11/1989 | Hashimoto et al. | 514/259 |

FOREIGN PATENT DOCUMENTS

| | | |
|---|---|---|
| 0129128 | 12/1984 | European Pat. Off. |
| 129128 | 12/1984 | European Pat. Off. |
| 0150411 | 8/1985 | European Pat. Off. |
| 524634 | 1/1993 | European Pat. Off. |
| 1485847 | 5/1967 | France |
| 1503564 | 10/1967 | France |
| 1545632 | 8/1969 | Germany |
| 151308 | 10/1981 | Germany |
| 232702 | 9/1982 | Germany |
| 3712782 | 11/1988 | Germany |
| 57-146741 | 9/1982 | Japan |
| 60-255752 | 12/1985 | Japan |
| 62-96476 | 5/1987 | Japan |
| 532610 | 2/1993 | Japan |
| 2163743 | 5/1986 | United Kingdom |

OTHER PUBLICATIONS

Chemical Abstracts, vol. 96, No. 1, Jan. 4, 1982, Bitter et al. Babad et al., "The Chemistry of Phosgene," *Chemical Reviews*, vol. 73, No. 1, pp. 75–91, 1973.

Temple et al., "The Preparation of 9-Amino-9H-purines. II. 9-Amino-6-chloro-9H-purin-8(7H)-one," *The Journal of Organic Chemistry*, Feb. 1968, vol. 33, No. 2, pp. 530–533.

King et al., "Reaction of Pyridine with Phosgene: A Structural Reevaluation," *The Journal of Organic Chemistry*, 1968, vol. 53, No. 26, pp. 6145–6147.

King et al., "An Unusually Facile Formation of Substituted 1,2-Dihydropyridine Derivatives: The Reversible Condensation of Pyridines with Reactive Carbonyl Groups," *J. Am. Chem. Soc.*, 1988, vol. 110, No. 17, pp. 5764–5767.

*Primary Examiner*—Matthew V. Grumbling
*Attorney, Agent, or Firm*—Sughrue, Mion, Zinn, Macpeak & Seas, PLLC

[57] ABSTRACT

A process for producing an dioxoquinazoline of following formula (II):

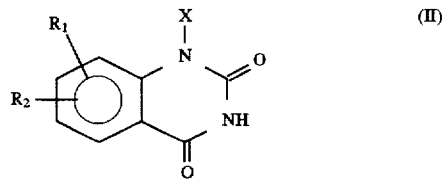

wherein $R_1$ and $R_2$ independently represent a hydrogen atom, a halogen atom, a nitro group, a lower alkyl group, an aralkyl group, an alkoxy group, an alkoxylcarbonyl group or a group represented by $YNR_3R_4$, wherein Y represents a direct bond, a lower alkylene group or a carbonyl group, and $R_3$ and $R_4$ independently represent a lower alkyl group or N, $R_3$ and $R_4$ may bond together to form a five- or six-membered heterocycle which comprises reacting an anthranylamide of formula (I):

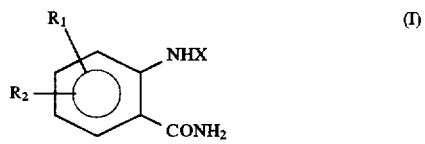

wherein X, $R_1$ and $R_2$ are as defined above.

12 Claims, No Drawings

PROCESS FOR PRODUCING DIOXOQUINAZOLINES

The present invention relates to a process for producing dioxoquinazolines. More particularly, it relates to a process for producing a dioxoquinazoline which comprises reacting an anthranylamide, corresponding to the dioxoquinazoline, with a reaction product of a pyridine and phosgene.

Dioxoquinazolines are useful as an intermediate for antiphlogistic, remedy for diabetic complication, etc. It is also known that dioxoquinazolines are produced by reacting anthranylamides with carbonyldiimidazole (e.g. JP-A-62-96476).

However, this process had a problem that the expensive carbonylimidazole is used as a reactant.

The present inventors have intensively studied about the process in which inexpensive phosgene is used instead of a carbonyldiimidazole so as to solve the problem. As a result, it has been found that the objective product can easily be produced when a reaction product of a pyridine and phosgene is used as the reactant, although the objective product cannot be obtained at all by using only phosgene as it is as the reactant. The present inventors have conducted further studies based on this finding and have completed the present invention.

That is, the present invention provides a process for producing an dioxoquinazoline represented by the following formula

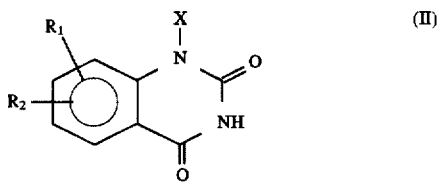

(II)

wherein $R_1$ and $R_2$ independently represent a hydrogen atom, a halogen atom, a nitro group, a lower alkyl group which is optionally substituted with one or more halogen atoms, an aralkyl group which is optionally substituted with one or more halogen atoms, a lower alkoxy group which is optionally substituted with one or more halogen atoms, a lower alkoxylcarbonyl group which is optionally substituted with one or more halogen atoms or a group represented by $YNR_3R_4$, wherein Y represents a direct bond, a lower alkylene group or a carbonyl group, and $R_3$ and $R_4$ independently represent a lower alkyl group or N, $R_3$ and $R_4$ may bond together to form a five- or six-membered heterocycle which optionally contains another hetero atom, said heterocycle being optionally substituted, and X represents a hydrogen atom, a lower alkyl group which is optionally substituted with one or more halogen atoms, an aralkyl group which is optionally substituted with a halogen atom or a group represented by $ZCO_2R_5$, wherein Z represents a lower alkylene group and $R_5$ represents a lower alkyl group or an aralkyl group, which comprises reacting an anthranylamide represented by the following formula (I):

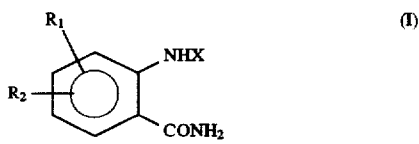

(I)

wherein X, $R_1$ and $R_2$ are as defined above, with a reaction product of a pyridine and phosgene.

Hereinafter, the present invention will be described in detail.

Examples of pyridines used as one of starting materials include pyridine, 2-picoline, 3-picoline, 4-picoline, 2-chloropyridine, 3-chloropyridine, 4-chloropyridine, 2,4-lutidine and 2,6-lutidine. Among them, pyridine is preferably used.

The reaction product of a pyridine and phosgene is usually produced, for example, by introducing phosgene to a mixture of a pyridine and an organic solvent; adding phosgene to an organic solvent, followed by adding a pyridine thereto; adding pyridine to an organic solvent while introducing phosgene thereto; or the like.

As the organic solvent, those inert to the reaction can be used. Examples of the solvent include cyclic ethers such as tetrahydrofuran and dioxane; glymes such as ethylene glycol dimethyl ether and diethylene glycol dimethyl ether; aromatic hydrocarbons such as benzene, toluene and xylene; aliphatic hydrocarbons such as hexane, heptane, octane and cyclohexane; halogenated hydrocarbons such as dichloromethane, chloroform, carbon tetrachloride, 1,2-dichloroethane, monochlorobenzene and dichlorobenzene; aliphatic esters such as ethyl acetate and butyl acetate; and aliphatic nitriles such as acetonitrile. Among them, cyclic ethers, glymes and aromatic hydrocarbons are preferred. Among the preferred examples, cyclic ethers are more preferred and particularly tetrahydrofuran is preferred. Amount of the organic solvent used is usually from 0.5 to 40-fold amount by weight, preferably from 1 to 20-fold amount by weight, based on the amount of the pyridine.

Phosgene may be introduced in a vapor state or introduced in a liquid state under elevated pressure. It is also possible to introduce phosgene dissolved in the organic solvent.

Amount of phosgene introduced is usually from about 0.1 to 2-fold molar amount, preferably from about 0.3 to 1.5-fold molar amount, based on the amount of the pyridine. An introducing inlet of phosgene may be at the vapor phase part or liquid phase part of the reactor. In the latter case, the reaction products are sometimes deposited close to the introducing inlet and, therefore, the reaction must be carried out taking this point into consideration.

The reaction of a pyridine and phosgene is usually carried out at a temperature of from about −10° to 60° C., preferably from about 0° to 50° C.

The substituents $R_1$ and $R_2$ in anthranylamide (I), which are same or different, are a hydrogen atom, a halogen atom, a nitro group, a lower alkyl group which is optionally substituted with one or more halogen atoms, an aralkyl group which is optionally substituted with one or more halogen atoms, a lower alkoxy group which is optionally substituted with one or more halogen atoms, a lower alkoxylcarbonyl group which is optionally substituted with a halogen atom or a group represented by $YNR_3R_4$, wherein Y represents a direct bond, a lower alkylene group or a carbonyl group, and $R_3$ and $R_4$, which are same or different, are a lower alkyl group or N, $R_3$ and $R_4$, may bond together to form a five- or six-membered heterocycle which optionally contains another hetero atom, said heterocycle being optionally substituted.

The substituents X in anthranylamide (I) is a hydrogen atom, a lower alkyl group which is optionally substituted with one or more halogen atoms, an aralkyl group which is optionally substituted with a halogen atom or a group represented by $ZCO_2R_5$, wherein Z represents a lower alkylene group and $R_5$ represents a lower alkyl group or an aralkyl group.

Examples of the halogen atom include chlorine, bromine and fluorine.

In the present specification, groups referred to as "lower" preferably contain from 1 to 5 carbon atoms. Lower alkoxycarbonyl means a lower alkoxy group bonded to a carbonyl group.

Examples of the lower alkyl group which is optionally substituted with one or more halogen atoms, as $R_1$, $R_2$ and X, include a lower alkyl group such as methyl, ethyl, propyl, i-propyl, butyl, i-butyl, t-butyl, pentyl, i-pentyl and hexyl; a monohalo lower alkyl group such as chloromethyl, bromomethyl and chloropropyl; a dihalo lower alkyl group such as 1,2-dichloroethyl, 1,2-dibromethyl and 2,2-dichloroethyl; and trihalo lower alkyl group such as trifluoromethyl.

Examples of the aralkyl group which is optionally substituted with one or more halogen atoms, as $R_1$, $R_2$ and X, include benzyl, phenylethyl, 4-chlorobenzyl, 2,4-dichlorobenzyl and 2,4-dibromobenzyl.

Examples of the unsubstituted lower alkoxy group, as $R_1$ and $R_2$, include methoxy, ethoxy, propoxy, i-propoxy, butoxy, i-butoxy, t-butoxy, pentyloxy, i-pentyloxy and hexyloxy. Examples of the lower alkoxy group substituted with the halogen atom, as $R_1$ and $R_2$, include chloromethoxy, bromomethoxy, 1-chloroethoxy, 2-chloroethoxy, 1-chloropropoxy, 2-chloropropoxy, 3-chloropropoxy, dichloromethexy, dibromomethoxy, 1,2-dichloroethoxy, 2,2-dichloroethoxy and trifluoroethoxy.

Examples of the lower alkoxycarbonyl group which is optionally substituted with one or more halogen atoms, as $R_1$ and $R_2$, include a carbonyl group substituted with the above-exemplified unsubstituted lower alkoxy group or lower alkoxy group substituted with one or more halogen atoms.

Examples of the lower alkylene group as Y include methylene, dimethylene, trimethylene and tetramethylene. Examples of the lower alkyl group as $R_3$ and $R_4$ include lower alkyl groups same to those exemplified above as $R_1$ and $R_2$. Specific examples of $YNR_3R_4$ include dimethylamino, diethylamino, dipropylamino and dibutylamino.

Specific examples of the case that N, $R_3$ and $R_4$ in $NR_3R_4$ bond together to form a five- or six-membered heterocycle which optionally have another hetero atom are pyrrolyl, 2H,4H-pyrrolyl, pyrrolidino, pyrazolyl, piperidino, morpholino and imidazolyl.

Examples of the substituent on N include the above-exemplified lower alkyl groups which are optionally substituted with one or more halogen atoms, the above-exemplified aralkyl groups which are optionally substituted with one or more halogen atoms, an aralkyl group substituted with a lower alkoxy group and a phenylcarbonyl group which is optionally substituted with a lower alkoxy group.

Examples of the lower alkylene group as Z include straight chain or branched lower alkylene group, such as methylene, methylmethylene, dimethylene, 2-methyldimethylene, trimethylene, tetramethylene, pentamethylene and hexamethylene. Among them, methylene and methylmethylene are preferred. Examples of a lower alkyl group and an aralkyl group as $R_5$ include a lower alkyl group and an aralkyl group, respectively, same to those exemplified above as $R_1$ and $R_2$.

Examples of the anthranylamides (I) include anthranylamide, 3-, 4-, 5-, 6-chloroanthranylamide, 3-, 4-, 5-, 6-bromo-anthranylamide, 3-, 4-, 5-, 6-fluoroanthranylamide, 3,4-, 3,5-, 3,6-, 4,5-, 4,6-, 5,6-dichloroanthranylamide, 3,4-, 3,5-, 3,6-, 4,5-, 4,6-, 5,6-dibromoanthanylamide, 3,4-, 3,5-, 3,6-, 4,5-, 4,6-, 5,6-difluoroanthranylamide, 3-bromo-4-chloroanthranylamide, 3-bromo-5-chloroanthranylamide, 3-bromo-6-chloroanthranylamide, 4-bromo-3-chloroanthranylamide, 4-bromo-5-chloroanthranylamide, 4-bromo-6-chloroanthranylamide, 5- bromo-3- chloroanthranylamide, 5-bromo-4-chloroanthranylamide, 5-bromo-6-chloroanthranylamide, 6-bromo-3-chloroanthranylamide, 6-bromo-4-chloroanthranylamide, 6-bromo-5-chloroanthranylamide, 3-chloro-4-fluoroanthranylamide, 3-bromo-4-fluoroanthranylamide, 3,4,5-, 3,4,6-, 3,5,6-, 4,5,6-trichloroanthranylamide, 3,4,5-, 3,4,6-, 3,5,6-, 4,5,6-tribromoanthranylamide, 3,4,5-, 3,4,6-, 3,5,6-, 4,5,6-trifluoroanthranylamide, 3-, 4-, 5-, 6-nitroanthranylamide, 3,4-, 3,5-,3,6-, 4,5-, 4,6-, 5,6-dinitroanthranylamide, 3-, 4-, 5-, 6-methylanthranylamide, 3-, 4-, 5-, 6-ethylanthranylamide, 3-, 4-, 5-, 6-chloromethylanthranylamide, 3-, 4-, 5-, 6-(chloromethoxy)anthranylamide, 3-, 4-, 5-, 6-(bromomethoxy)anthranylamide, 3-, 4-, 5-, 6-(1-chloroethoxy)anthranylamide, 3-, 4-, 5-, 6-(2-chloroethoxy) anthranylamide, 3,4-dimethylanthranylamide, 3,4-diethylanthranylamide, 3-propoxyanthranylamide, 3-i-propoxyanthranylamide, 5,6-dimethoxyanthranylamide, 3,5-diethoxyanthranylamide, 3,6-dipropoxyanthranylamide, 3-, 4-, 5-, 6-benzylanthranylamide, 3-, 4-, 5-, 6-(4chlorobenzyl)anthranylamide, 3-, 4-, 5-, 6-(4-bromobenzyl)anthranylamide, 3-(2-phenylethyl) anthranylamide, 3-(2,4-dichlorobenzyl)anthranylamide, 3-(2,4-dibromobenzyl)-anthranylamide, 3-methoxyanthranylarmide, 3-, 4-, 5-, 6-(N,N-dimethylamino)anthranylamide' 3-, 4-, 5-, 6-(N,N-diethylamino)anthranylamide, 3-, 4-, 5-, 6-(1-pyrrolyl) anthranylamide, 3-, 4-, 5-, 6-(2H,4H-pyrrolyl) anthranylamide, 3-, 4-, 5-, 6-(1-imidazolyl) anthranylamide, 3-, 4-, 5-, 6-(1-pyrazolyl) anthranylamide, 3-, 4-, 5-, 6-(piperidino) anthranylamide, 3-, 4-, 5-, 6-(morpholino) anthranylamide, 3-, 4-, 5-, 6-(4-methylpiperidino) anthranylamide, N-methylanthranylamide, 3-, 4-, 5-, 6-chloro-N-methylanthranylamide, 3-, 4-, 5-, 6-bromo-N-methylanthranylamide, 3-, 4-, 5-, 6-fluoro-N-methylanthranylamide, N-ethylanthranylamide, 3-, 4-, 5-, 6-chloro-N-ethylanthranylamide, 3-, 4-, 5-, 6-bromo-N-ethylanthranylamide, 3-, 4-, 5-, 6-fluoro-N-ethylanthranylamide, N-(chloromethyl)anthranylamide, N-(2-chloroethyl)anthranylamide, methyl N-(2-carbamoylphenyl)aminoacetate, ethyl N-(2-carbamoylphenyl)aminoacetate, propyl N-(2-carbamoylphenyl)aminoacetate, i-propyl N-(2-carbamoylphenyl)aminoacetate, butyl N-(2-carbamoylphenyl)aminoacetate, t-butyl N-(2-carbamoylphenyl) aminoacetate, benzyl N-(2-carbamoylphenyl)aminoacetate, methyl N-(2-carbamoyl-5-chlorophenyl)aminoacetate, ethyl N-(2-carbamoyl-5-chlorophenyl)aminoacetate, propyl N-(2-carbamoyl-5-chlorophenyl) aminoacetate, i-propyl N-(2-carbamoyl-5-chlorophenyl)aminoacetate, butyl N-(2-carbamoyl-5-chlorophenyl)aminoacetate, t-butyl N-(2-carbamoyl-5-chlorophenyl) aminoacetate and benzyl N- (2-carbamoyl-5-chlorophenyl)aminoacetate.

Reaction of the anthranylamide with a reaction product of a pyridine and phosgene is usually carried out by adding an anthranylamide (I) or a mixture thereof with a solvent to the reaction product of a pyridine and phosgene. The solvent includes an organic solvent inert to the reaction. Examples of the solvent include the above-exemplified organic solvents used for the reaction of a pyridine and phosgene, but the solvent may be different from the solvent used for the reaction of a pyridine and phosgene. Amount of the organic solvent, if used, is usually from 0.5 to 50-fold amount by weight, preferably from 1 to 20-fold amount by weight, based on the amount of the anthranylamide (I).

Amount of the reaction product of a pyridine and phosgene is usually from about 1 to 20-fold amount by molar, preferably from about 2 to 12-fold amount by molar, calculated based on pyridine relative to the amount of the anthranylamide (I).

Reaction of the anthranylamide with a reaction product of a pyridine and phosgene is usually carried out at a temperature of from about 0° to 100° C., preferably from about 20° to 80° C.

It is preferred that an amine is added to the reaction together with the anthranylamide (I) or after the anthranylamide (I) is added in order to accelerate the reaction. This measure is particularly effective when the phosgene is used in an amount of from 0.5 to 1.5-fold by molar per the amount of the pyridine. Examples of the amines used for this purpose include pyridines such as pyridine, 2-picoline, 3-picoline, 4-picoline, 2-chloropyridine, 3chloropyridine, 4-chloropyridine, 2,4-lutidine and 2,6-lutidine; and tertiary amines such as triethylamine, tributylamine, ethyldiisopropylamine, N,N-dimethylaniline and N,N-diethylaniline.

Amount of the amine is usually from about 0.1 to 5-fold amount by molar, preferably from about 0.3 to 2-fold amount by molar based on the amount of phosgene used in the reaction of a pyridine and phosgene.

When the desired products are removed from the reaction mixture, it is usual that the reaction product of a pyridine and phosgene remaining is first removed. Examples of such a removing process include a process of adding a base. When the pyridine is used at a rate of 2-fold molds or more based on phosgene, a process of adding water or an aqueous acid solution may also be employed. Dioxoquinazoline (II) can be obtained from the reaction mixture after the removing step by distilling off a part or whole of the organic solvent, followed by subjecting the mixture to separating means such as filtration.

The resulting dioxoquinazoline (II) can be purified further, if necessary.

According to the present invention, dioxoquinazolines (II) can be produced easily using a reaction product of a pyridine and phosgene, which is inexpensive. Therefore, the process of the present invention is advantageous from the industrial view.

The following Examples further illustrate the present invention in detail but are not to be construed to limit the scope thereof.

EXAMPLE 1

To a 100 ml flask equipped with a refrigerator (−20° C.), 25 g of tetrahydrofuran and 7.9 g of pyridine were charged under a nitrogen atmosphere and the mixture was cooled to 5° C. Then, phosgene was introduced to the vapor phase part at a flow rate of 0.2 g/min. for 20 minutes.

After the reaction mixture was heated to 45° C., a mixture of 2.57 g ethyl N-(2-carbamoyl-5-chlorophenyl) aminoacetate and 25 g of tetrahydrofuran was added thereto over 2 hours, followed by stirring the mixture for 3 hours while keeping the temperature at 45° C.

After the completion of the reaction, water was added to the reaction mixture which was then analyzed by high-performance liquid chromatography. Result of the analysis showed that the conversion of ethyl N-(2-carbamoyl-5-chlorophenyl)aminoacetate was 100% and that 1.98 g of ethyl 2-(7-chloro-1,2,3,4-tetrahydro-2,4-dioxoquinazoline-1-yl)acetate was produced (Yield: 70%).

Thereafter, the reaction mixture was concentrated under reduced pressure to precipitate the solid component. The solid component was filtered and re-crystallized from N-methylpyrrolidone to obtain 1.48 g of 2-(7-chloro-1,2,3,4tetrahydro-2,4-dioxoquinazoline-1-yl)acetone. (Purity 98%)

EXAMPLE 2

To a 300 ml flask equipped with a refrigerator (−20° C.), 46 g of tetrahydrofuran and 30 g of pyridine were charged under a nitrogen atmosphere and the mixture was cooled to 5° C. Then, phosgene was introduced to the vapor phase part at a flow rate of 0.4 g/min. for 37 minutes.

After the reaction mixture was heated to 60° C., a mixture of 15.4 g N-(2-carbamoyl-5-chlorophenyl)aminoacetate and 77 g of tetrahydrofuran was added thereto over 40 minutes while keeping the temperature at 60° C., followed by stirring the mixture for 2 more hours while keeping the temperature at 60° C.

After the completion of the reaction, water was added to the reaction mixture which was then analyzed by high-performance liquid chromatography. Result of the analysis showed that the conversion of ethyl N-(2-carbamoyl-5-chlorophenyl)aminoacetate was 100% and that 13.7 g of ethyl 2-(7-chloro-1,2,3,4tetrahydro-2,4-dioxoquinazoline-1-yl)acetate was produced (Yield: 81%).

EXAMPLE 3

To a 100 ml flask equipped with a refrigerator (−20° C.), 13 g of tetrahydrofuran and 3.9 g of pyridine were charged under a nitrogen atmosphere and the mixture was cooled to 5° C. Then, phosgene was introduced to the vapor phase part at a flow rate of 0.2 g/min. for 10 minutes.

After the reaction mixture was heated to 45° C., a mixture of 2.57 g ethyl N-(2-carbamoyl-5-chlorophenyl) aminoacetate and 25 g of tetrahydrofuran was added thereto over 2 hours, followed by stirring the mixture for 3 more hours while keeping the temperature at 45° C.

After the completion of the reaction, water was added to the reaction mixture which was then analyzed by high-performance liquid chromatography. Result of the analysis showed that the conversion of ethyl N-(2-carbamoyl-5-chlorophenyl)aminoacetate was 100% and that 1.73 g of ethyl 2-(7-chloro-1,2,3,4-tetrahydro-2,4-dioxoquinazoline-1-yl) acetate was produced (Yield: 61%).

EXAMPLE 4

To a 300 ml flask equipped with a refrigerator (−20° C.), 46 g of tetrahydrofuran and 15 g of pyridine were charged under a nitrogen atmosphere and the mixture was cooled to 5° C. Then, phosgene was introduced to the vapor phase part at a flow rate of 0.4 g/min. for 37 minutes.

After the reaction mixture was heated to 60° C., a mixture of 15.4 g ethyl N-(2-carbamoyl-5-chlorophenyl) aminoacetate and 77 g of tetrahydrofuran was added thereto over 40 minutes while keeping the temperature at 60° C., followed by keeping the temperature at 60° C. for 30 more minutes.

Then, 15 g of pyridine was added to the reaction mixture over 20 minutes and the solution was kept at 60° C. for 1 more hour.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 98% and that 15.6 g of ethyl 2-(7-chloro-1,2,3,4tetrahydro-2,4-dioxoquinazoline-1-yl) acetate was produced (Yield: 92%).

EXAMPLE 5

To a 300 ml flask equipped with a refrigerator (−20° C.), 77 g of tetrahydrofuran and 12 g of pyridine were charged under a nitrogen atmosphere and the mixture was cooled to 5° C. Then, phosgene was introduced to the vapor phase part at a flow rate of 0.4 g/min. for 30 minutes.

After the reaction mixture was heated to 45° C., a mixture of 7.7 g ethyl N-(2-carbamoyl-5-chlorophenyl)aminoacetate and 62 g of tetrahydrofuran was added thereto over 2 hours, followed by keeping the mixture for 30 more minutes at the temperature of 45° C.

After the temperature was raised to 45° C., 15 g of triethylamine and 15 g of THF were added over 30 minutes, followed by keeping the temperature at 45° C. for 30 more minutes.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 98% and that 6 g of ethyl 2-(7-chloro-1,2,3,4-tetrahydro-2,-4-dioxoquinazoline-1-yl) acetate was produced (Yield: 71%).

EXAMPLE 6

To a 500 ml flask equipped with a refrigerator (−20° C.), 154 g of toluene and 24 g of pyridine were charged under a nitrogen atmosphere and the mixture was cooled to 5° C. Then, phosgene was introduced to the vapor phase part at a flow rate of 0.4 g/min. for 60 minutes.

After the reaction mixture was heated to 60° C., a mixture of 15.4 g ethyl N-(2-carbamoyl-5-chlorophenyl) aminoacetate and 154 g of toluene was added dropwise thereto over 40 minutes while keeping the temperature at 60° C., followed by keeping the mixture for 30 more minutes at the temperature of 60° C.

Then, a mixed solution of 24 g of pyridine and 31 g of toluene was added dropwise over 30 minutes, followed by keeping the temperature at 60° C. for 30 more minutes.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 99% and that 12.9 g of ethyl 2-(7-chloro-1,2,3,4-tetrahydro-2,4-dioxoquinazoline-1-yl) acetate was produced (Yield: 76%).

EXAMPLE 7

To a 500 ml flask equipped with a refrigerator (−20° C.), 77 g of toluene and 15 g of pyridine were charged under a nitrogen atmosphere and the mixture was cooled to 5° C. Then, phosgene was introduced to the vapor phase part at a flow rate of 0.4 g/min. for 37 minutes.

After the reaction mixture was heated to 60° C., a mixture of 15.4 g ethyl N-(2-carbamoyl-5-chlorophenyl) aminoacetate, 15 g of pyridine and 154 g of toluene was added dropwise thereto over 90 minutes while keeping the temperature at 60° C., followed by keeping the mixture for 45 more minutes at the temperature of 60° C.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 99% and that 13.2 g of ethyl 2-(7-chloro-1,2,3,4tetrahydro-2,4-dioxoquinazoline-1-yl) acetate was produced (Yield: 78%).

EXAMPLE 8

To a 300 ml flask equipped with a refrigerator (−20° C.), 66 g of diglyme and 10 g of pyridine were charged under a nitrogen atmosphere and the mixture was cooled to 5° C. Then, phosgene was introduced to the vapor phase part at a flow rate of 0.2 g/min. for 50 minutes.

After the reaction mixture was heated to 45° C., a mixture of 7.7 g ethyl N-(2-carbamoyl-5-chlorophenyl)aminoacetate and 62 g of diglyme was added dropwise thereto over 40 minutes while keeping the temperature at 45° C., followed by keeping the mixture for 30 more minutes at the temperature of 45° C.

Then, a mixed solution of 10 g of pyridine and 13 g of diglyme was added dropwise over 20 minutes, followed by keeping the temperature at 45° C. for 1 more hour.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 100% and that 7.5 g of ethyl 2-(1-chloro-1,2,3,4-tetrahydro-2,4-dioxoquinazoline-1-yl) acetate was produced (Yield: 89%).

EXAMPLE 9

To a 300 ml flask equipped with a refrigerator (−20° C.), 77 g of tetrahydrofuran, 77 g of toluene and 24 g of pyridine were charged under a nitrogen atmosphere and the mixture was cooled to 5° C. Then, phosgene was introduced to the vapor phase part at a flow rate of 0.4 g/min. for 60 minutes.

After the reaction mixture was heated to 45° C., a mixture of 15.4 g ethyl N-(2-carbamoyl-5-chlorophenyl) aminoacetate, 77 g of tetrahydrofuran and 77 g of toluene was added dropwise thereto over 40 minutes, followed by keeping the mixture for 60 more minutes at the temperature of 60° C.

Then, a mixed solution of 24 g of pyridine and 31 g of toluene was added dropwise over 20 minutes, followed by keeping the temperature at 60° C. for 30 more minutes.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 100% and that 14.9 g of ethyl 2-(7-chloro-1,2,3,4-tetrahydro-2,4-dioxoquinazoline-1-yl)acetate was produced (Yield: 88%).

COMPARATIVE EXAMPLE 1

To a 100 ml flask equipped with a refrigerator (−20° C.), 13 g of tetrahydrofuran wee charged under a nitrogen atmosphere and the mixture was cooled to 5° C. Then, phosgene was introduced to the vapor phase part at a flow rate of 0.2 g/min. for 10 minutes.

Thereafter, a mixture of 2.57 g ethyl N-(2-carbamoyl-5-chlorophenyl)aminoacetate and 25 g of tetrahydrofuran was added thereto. Then, the mixture was heated to 45° C., followed by keeping the mixture at the same temperature for 3 hours.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 75.9%, and that ethyl 2-(7-chloro-1,2,3,4-tetrahydro-2,4-dioxoquinazoline-1-yl)acetate was not produced at all.

COMPARATIVE EXAMPLE 2

To a 100 ml flask equipped with a refrigerator (−20° C.), 13 g of tetrahydrofuran was charged under a nitrogen atmosphere and the mixture was cooled to 5° C. Then, phosgene was introduced to the vapor phase part at a flow rate of 0.2 g/min. for 10 minutes.

Thereafter, a mixture of 2.57 g ethyl N-(2-carbamoyl-5-chlorophenyl)aminoacetate and 25 g of tetrahydrofuran was added thereto. Then, after the reaction mixture was heated to 45° C., 3.9 g of pyridine added, followed by keeping the reaction mixture at the same temperature for 3 hours.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 90.6%, and that ethyl 2-(7-chloro-1,2,3,4-tetrahydro-2,4dioxoquinazoline-1-yl)acetate was not produced at all.

COMPARATIVE EXAMPLE 3

To a 100 ml flask equipped with a refrigerator (−20° C.), 13 g of tetrahydrofuran, 2.57 g ethyl N-(2-carbamoyl-5chlorophenyl)aminoacetate and 3.9 g of pyridine were charged under a nitrogen atmosphere and the mixture was cooled to 5° C. Then, phosgene was introduced to the vapor phase part at a flow rate of 0.2 g/min. for 10 minutes.

Thereafter, the mixture was heated to 45° C., followed by keeping the reaction mixture at the same temperature for 3 hours.

After the completion of the reaction, water was added to the reaction mixture which was then analyzed by high-performance liquid chromatography. Results of the analysis showed that the conversion of ethyl N-(2-carbamoyl-5-chlorophenyl)aminoacetate was 9.8% and that the yield of ethyl 2-(7-chloro-1,2,3,4-tetrahydro-2,4-dioxoquinazoline-1-yl)acetate was 2%.

What we claim is:

1. A process for producing an dioxoquinazoline represented by the following formula (II):

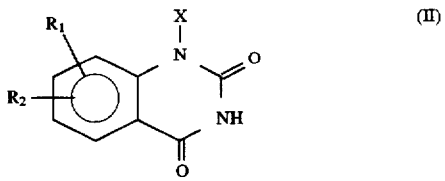

wherein $R_1$ and $R_2$ independently represent a hydrogen atom, a halogen atom, a nitro group, a lower alkyl group which is optionally substituted with one or more halogen atoms, an aralkyl group which is optionally substituted with one or more halogen atoms, an alkoxy group which is optionally substituted with one or more halogen atoms, an alkoxylcarbonyl group which is optionally substituted with one or more halogen atoms or a group represented by $YNR_3R_4$, wherein Y represents a direct bond, a lower alkylene group or a carbonyl group, and $R_3$ and $R_4$ independently represent a lower alkyl group or N, $R_3$ and $R_4$ may bond together to form a five- or six-membered heterocycle which optionally contains another hetero atom, said heterocycle being optionally substituted, and X represents a hydrogen atom, a lower alkyl group which is optionally substituted with one or more halogen atoms, an aralkyl group which is optionally substituted with one or more halogen atoms or a group represented by $ZCO_2R_5$, wherein Z represents a lower alkylene group and $R_5$ represents a lower alkyl group or an aralkyl group which comprises reacting an anthranylamide represented by the following formula (I):

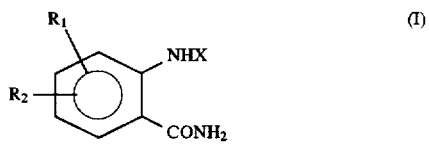

wherein X, $R_1$ and $R_2$ are as defined above, with a reaction product of a pyridine and phosgene.

2. A process according to claim 1 wherein first a pyridine and phosgene are reacted and then the anthranylemide is added to the reaction mixture.

3. A process according to claim 1 wherein the amount of the pyridine on a molar basis is 1–20-fold based on the amount of the anthranylamide of formula (I).

4. A process according to claim 1 wherein the amount of phosgene on a molar basis is 0.1–2-fold based on the amount of the pyridine.

5. A process according to claim 2 wherein an amine is added to the reaction mixture together with or after the anthranylamide of formula (I) is added.

6. A process according to claim 5 wherein the amount of amine on a molar basis is 0.1–5-fold based on the amount of the phosgene.

7. A process according to claim 6 wherein the amine is a pyridine or a tertiary amine.

8. A process according to claim 1 wherein the pyridine is at least one selected from pyridine, 2-picoline, 3-picoline, 4-picoline, 2-chloropyridine, 3-chloropyridine, 4-chloropyridine, 2,4-lutidine and 2,6-lutidine.

9. A process according to claim 7 wherein the tertiary amine is at least one selected from triethylamine, tributylamine, ethyldiisopropylamine, N,N-dimethylaniline and N,N-diethylaniline.

10. A process according to claim 1 wherein the reaction is carried out in the presence of an organic solvent.

11. A process according to claim 10 wherein the organic solvent is at least one solvent selected from a group consisting of cyclic ethers, glymes, aromatic hydrocarbons, aliphatic hydrocyclic, halogenated hydrocarbons, aliphatic esters and aliphatic nitrites.

12. A process according to claim 7 wherein the pyridine is at least one selected from pyridine, 2-picoline, 3-picoline, 4-picoline, 2-chloro-pyridine, 3-chloropyridine, 4-chloropyridine, 2,4-lutidine and 2,6-lutidine.

* * * * *